United States Patent [19]

Michel et al.

[11] 4,442,295
[45] Apr. 10, 1984

[54] 3-CYANO INDOLES AS INTERMEDIATES FOR CARDIOSELECTIVE COMPOUNDS

[75] Inventors: Helmut Michel, Mannheim; Wolfgang Kampe, Heddesheim; Roland Ofenloch, Lorsch, all of Fed. Rep. of Germany

[73] Assignee: Boehringer Mannheim GmbH, Mannheim, Fed. Rep. of Germany

[21] Appl. No.: 288,077

[22] Filed: Jul. 29, 1981

[30] Foreign Application Priority Data

Aug. 8, 1980 [DE] Fed. Rep. of Germany ....... 3029980

[51] Int. Cl.³ .......................................... C07D 209/04
[52] U.S. Cl. .................................. 548/505; 548/492; 548/493; 548/495
[58] Field of Search .................. 260/326.16; 548/492, 548/493, 495, 504

[56] References Cited

U.S. PATENT DOCUMENTS 3,072,530  1/1963  Hofmann et al. ............... 260/326.16
3,226,399 12/1965  Allen et al. ........................ 548/492

FOREIGN PATENT DOCUMENTS 1905881 9/1969 Fed. Rep. of Germany ........................ 260/326.16
2626890 12/1977 Fed. Rep. of Germany ....... 548/492

OTHER PUBLICATIONS

Can. J. Chem., 42, 514/1964.

Primary Examiner—Donald G. Daus
Assistant Examiner—G. Hendrick

Attorney, Agent, or Firm—Sprung, Horn, Kramer & Woods

[57] ABSTRACT

The present invention provides indole derivatives of the general formula:

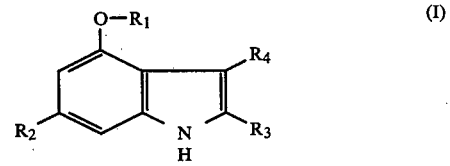

wherein $R_1$ is a hydrogen atom, an aralkyl radical or a radical of the general formula:

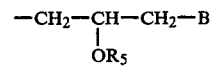

in which B is a reactive group or, together with $R_5$, represents a valency bond, and $R_5$ is a hydrogen atom or an aliphatic or aromatic acyl radical, $R_2$ is a hydrogen atom or a lower alkyl radical, $R_3$ is a hydrogen atom, a methyl radical or a $-CH_2-O-R_5$ radical, $R_5$ having the same meaning as above, and $R_4$ is an aminocarbonyl, cyano, oximinomethyl, formyl, hydroxymethyl or lower alkoxycarbimidoyl radical, with the proviso that $R_1$ is not an aralkyl radical when $R_4$ is a formyl radical. The present invention also provides processes for the preparation of these compounds. Furthermore, the present invention is concerned with the use of these compounds for the preparation of compounds with a heart and circulatory activity.

6 Claims, No Drawings

3-CYANO INDOLES AS INTERMEDIATES FOR CARDIOSELECTIVE COMPOUNDS

The present invention is concerned with new indole derivatives and with the preparation thereof.

The new indole derivatives according to the present invention are compounds of the general formula:

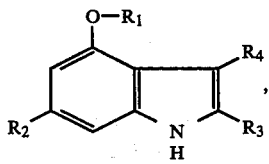

(I)

wherein $R_1$ is a hydrogen atom, an aralkyl radical or a radical of the general formula:

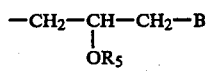

in which B is a reactive group or, together with $R_5$, represents a valency bond, and $R_5$ is a hydrogen atom or an aliphatic or aromatic acyl radical, $R_2$ is a hydrogen atom or a lower alkyl radical, $R_3$ is a hydrogen atom, a methyl radical or a —$CH_2$—O—$R_5$ radical, in which $R_5$ has the same meaning as above, and $R_4$ is an aminocarbonyl, cyano, oximinomethyl, formyl, hydroxymethyl or lower alkoxycarbimidoyl radical, with the proviso that $R_1$ is not an aralkyl radical when $R_4$ is a formyl radical.

An aralkyl radical $R_1$ is, according to the present invention, to be understood to be a radical, the aryl moiety of which is a phenyl radical and the alkyl moiety of which is a straight or branched-chained saturated hydrocarbon chain containing up to 4 carbon atoms, the benzyl radical being preferred.

The reactive group B can be a chlorine or bromine atom or a mesyloxy or tosyloxy radical.

The aliphatic or aromatic acyl radical $R_5$ is, according to the present invention, for example an acetyl, formyl or benzoyl radical.

The lower alkoxycarbimidoyl radical $R_4$ is preferably a methoxycarbimidoyl or ethoxycarbimidoyl radical.

The lower alkyl radical $R_2$ is to be understood to be a straight-chained or branched radical containing up to 6 and preferably up to b 4 carbon atoms, for example a methyl, ethyl, n-propyl, isopropyl, n-butyl, isobutyl, tert.-butyl or n-hexyl radical, the methyl and tert.-butyl radicals being especially preferred.

The new compounds of general formula (I) according to the present invention are useful intermediates for the preparation of compounds with valuable therapeutic properties, for example for the preparation of compounds of the general formula:

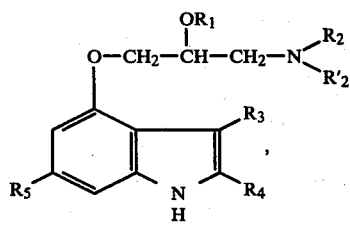

(II)

wherein $R_1$ is a hydrogen atom, a lower alkanoyl radical or an aroyl radical, $R_2$ is a lower alkyl radical or a radical of the general formula:

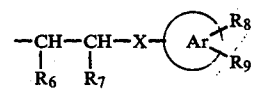

in which X is a valency bond, a methylene radical, or an oxygen or sulphur atom, Ar is a monocyclic, carbo- or heterocyclic aryl radical, $R_6$ and $R_7$, which can be the same or different, are hydrogen atoms or lower alkyl radicals, $R_8$ and $R_9$, which can be the same or different, are hydrogen or halogen atoms, hydroxyl groups, lower alkanoyl radicals, alkenyl radicals, alkynyl radicals, alkyl radicals, lower alkoxy radicals, aralkoxy radicals, alkenyloxy radicals, alkynyloxy radicals, lower alkylthio radicals, aminocarbonyl radicals, aminosulphonyl radicals or acylamino radicals or $R_2$ is a 1,4-benzodioxan-2-ylmethyl radical, $R'_2$ is a hydrogen atom or a benzyl radical, $R_3$ is a carboxyl, lower alkoxycarbonyl, aminocarbonyl, cyano, oximinomethyl, formyl, hydroxymethyl or lower alkoxycarbimidoyl radical, $R_4$ is a hydrogen atom, a lower alkyl radical or a —$CH_2$—O—$R_1$ radical, $R_1$ having the same meaning as above, and $R_5$ is a hydrogen atom or a lower alkyl radical; as well as of the pharmacologically acceptable salts thereof.

For this purpose, according to Application Ser. No. 288,075, filed July 29, 1981, now pending, the disclosure of which is incorporated herein by reference, a compound of general formula (I), in which $R_2$, $R_3$ and $R_4$ have the abovegiven meanings and $R_1$ is a radical of the general formula:

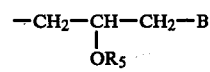

in which B is a reactive group or, together with $R_5$, represents a valency bond, is reacted in known manner with a compound of the general formula:

 (III), in which $R_2$ is a lower alkyl radical or a radical of the general formula:

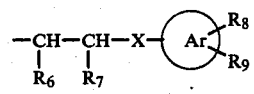

in which X is a valency bond, a methylene radical or an oxygen or sulphur atom, Ar is a monocyclic, carbo- or heterocyclic radical, $R_6$ and $R_7$, which can be the same or different, are hydrogen atoms or lower alkyl radicals, $R_8$ and $R_9$, which can be the same or different, are hydrogen or halogen atoms, hydroxyl groups, lower alkanoyl radicals, alkenyl radicals, alkynyl radicals, alkyl radicals, lower alkoxy radicals, aralkoxy radicals, alkenyloxy radicals, alkynyloxy radicals, lower alkylthio radicals, aminocarbonyl radicals, aminosulphonyl radicals or acylamino radicals, or $R_2$ is a 1,4-benzodioxan-2-ylmethyl radical, whereafter, if desired, one of the substituents $R_1$, $R'_2$, $R_3$, $R_4$ or $R_5$ in a compound obtained of general formula (II) is converted in known manner into another substituent $R_1$, $R'_2$, $R_3$, $R_4$ or $R_5$ having the above-given meanings, and the compounds obtained are, if desired, converted into their pharmacologically acceptable salts.

The compounds of general formula (II), as well as their pharmacologically acceptable salts, display an inhibition of the $\beta_1$-receptors and thus are outstandingly cardioselective. Therefore, they can be used for the treatment and prophylaxis of heart and circulatory diseases.

The compounds of general formula (I) according to the present invention can be prepared, for example, by one of the following processes:

(a) a compound of the general formula:

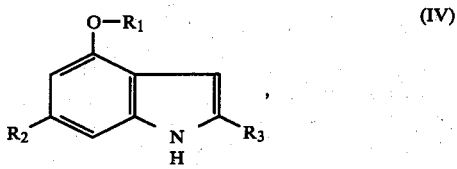

(IV)

in which $R_1$ is a hydrogen atom, an aralkyl radical or a

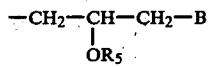

radical, B being a reactive group or, together with $R_5$, representing a valency bond and $R_5$ being a hydrogen atom or an aliphatic or aromatic acyl radical, $R_2$ is a hydrogen atom or a lower alkyl radical and $R_3$ is a hydrogen atom, a methyl radical or a $-CH_2-OR_5$ radical, $R_5$ having the same meaning as in general formula (I), is reacted with N-carbonylsulphamoyl chloride, which is also called chlorosulphonyl isocyanate, in an appropriate solvent, in known manner (see Chem. Ber., 100, 2719/1967; Synthesis, 1978, 374; and J. Chem. Soc., Perkin I, 1978, 1117); or (b) for the case in which $R_1$ in general formula (I) is a hydrogen atom or an aralkyl radical, a compound of general formula (IV), in which $R_1$ is a hydrogen atom or an aralkyl radical and $R_2$ and $R_3$ have the same meanings as in (a) above, is reacted with freshly prepared triphenylphosphine isothiocyanate in an appropriate solvent in known manner (see Tetrahedron Letters, 1977, 4417 or J. Chem. Soc., Perkin I, 1980, 1132); whereafter, if desired, one of the substituents $R_1$, $R_2$, $R_3$, $R_4$ or $R_5$ in a compound obtained of general formula (I) is converted in known manner into another substituent $R_1$, $R_2$, $R_3$, $R_4$ or $R_5$ having the meanings given above in general formula (I).

The processes according to the present invention are preferably carried out in a solvent which is inert under the reaction conditions, for example, water, methanol, ethanol, n-butanol, dioxan, acetonitrile, nitromethane, pyridine, dimethylformamide or methylene chloride, optionally in the presence of an acid-binding agent.

According to a preferred embodiment of process (a), the N-carbonylsulphamoyl chloride and the indole derivative of general formula (IV) are used in nitromethane or acetonitrile and the reaction mixture, after the addition of dimethylformamide, is treated with a tertiary amine.

The reactions according to process (a) are carried out with ice cooling, at ambient temperature or with warming, possibly under an atmosphere of a protective gas and the reactions according to process (b) are carried out at a temperature below $-20°$ C. under an atmosphere of a protective gas.

The starting materials used in the processes according to the present invention are, as a rule, compounds known from the literature. In general, new compounds are prepared in a manner analogous to that used for the preparation of the known compounds.

Examples of conversions of one of the substituents $R_1$, $R_2$, $R_3$, $R_4$ or $R_5$ in compounds of general formula (I) into other substituents $R_1$, $R_2$, $R_3$, $R_4$ or $R_5$ having the meanings given in general formula (I) include the following:

splitting off a benzyloxy radical to give a hydroxyl group;

alkylation of a hydroxyl group to give an epoxypropoxy compound;

dehydration of an aminocarbonyl or oximinomethyl radical to give a cyano group;

reduction of a formyl radical to give a hydroxymethyl radical; and conversion of a formyl radical into an oximinomethyl radical by reaction with hydroxylamine.

The following examples are given for the purpose of illustrating the present invention:

EXAMPLE 1

4-(2,3-Epoxypropoxy)-3-formylindole 9.9 g. 4-Hydroxy-3-formylindole (preparation see Example 3) are dissolved in 200 ml. ethanol and 100 ml. epichlorohydrin, mixed with 6.4 g. sodium methylate and stirred for 6 hours at ambient temperature. After evaporating off the solvent, the residue is stirred with water and diethyl ether, the ether phase is evaporated and the remaining crystals are filtered off with suction. There are obtained 6.7 g. (50% of theory) 4-(2,3-epoxypropoxy)-3-formylindole; m.p. 108°–110° C.

The following compounds are obtained in an analogous manner:

| | designation | yield % | m.p. (solvent) |
|---|---|---|---|
| (a) | 4-(2,3-epoxypropoxy)-3-hydroxymethylindole from 4-hydroxy-3-hydroxymethyl-indole (Example 3a) | 60 | oil |
| (b) | 4-(2,3-epoxypropoxy)-3-aminocarbonylindole from 4-hydroxy-3-aminocarbonyl-indole (Example 3b) | 80 | 70–75 (sinter point) (ethyl acetate) |
| (c) | 4-(2,3-epoxypropoxy)-3-cyanoindole from 4-hydroxy-3-cyanoindole (Example 3c) | 45 | 110–115 (diethyl ether) |

EXAMPLE 2

4-Benzyloxy-3-cyanoindole 2.7 g. 4-Benzyloxy-3-aminocarbonylindole (see Example 6) in 60 ml. anhydrous pyridine are mixed with 3.8 g. p-toluenesulphonyl chloride and, when the reaction is finished, the reaction mixture is dissolved in 2 N sulphuric acid. The acidic aqueous phase is extracted with diethyl ether. After evaporation of the ethereal solution, there are obtained 1.5 g. (60% of theory) 4-benzyloxy-3-cyanoindole; m.p. 139°–141° C.

The following compounds are obtained in an analogous manner:

| | designation | Yield % | m.p. (solvent) |
|---|---|---|---|
| (a) | 4-benzyloxy-3-cyanoindole from 4-benzyloxy-3-oximino-methylindole (Example 4) | 40 | 139–140 (diethyl ether) |
| (b) | 4-(2,3-epoxypropoxy)-3-cyanoindole from 4-(2,3-epoxypropoxy)-3-aminocarbonylindole (Example 1c) | 20 | 138–140 (diethyl ether) |

EXAMPLE 3

4-Hydroxy-3-formylindole 17.2 g. 4-Benzyloxy-3-formylindole (see Can. J. Chem., 42, 514/1964) are dissolved in 700 ml. methanol, 5 ml. triethylamine are added thereto and the reaction mixture is mixed with 3 g. 10% palladium-active charcoal and hydrogenated at ambient temperature and 1 bar hydrogen pressure. After removal of the catalyst, the reaction mixture is evaporated to give 11 g. (98% of theory) 4-hydroxy-3-formylindole; m.p. 196°–200° C.

The following compounds are obtained in an analogous manner:

| | designation | Yield % | m.p. (solvent) |
|---|---|---|---|
| (a) | 4-hydroxy-3-hydroxymethyl-indole from 4-benzyloxy-3-hydroxy-methylindole (Example 5) | 96 | oil |
| (b) | 4-hydroxy-3-aminocarbonyl-indole from 4-benzyloxy-3-aminocarbonyl-indole (Example 6) | 85 | 304–305 (methanol) |
| (c) | 4-hydroxy-3-cyanoindole from 4-benzyloxy-3-cyanoindole (Examples 2, 2a, 7) | 56 | 205–207 (methanol) |

EXAMPLE 4

4-Benzyloxy-3-oximinomethylindole

This compound is obtained in a yield of 96% of theory by reacting 4-benzyloxy-3-formylindole with hydroxylamine hydrochloride and sodium acetate in aqueous dimethylformamide solution; m.p. 206°–210° C.

EXAMPLE 5

4-Benzyloxy-3-hydroxymethylindole

This compound is obtained in a yield of 97% of theory by the reduction of 4-benzyloxy-3-formylindole with sodium borohydride in methanolic solution; m.p. 121°–123° C.

EXAMPLE 6

4-Benzyloxy-3-aminocarbonylindole 4.4 g. 4-Benzyloxyindole (see Helv. Chim. Acta, 54. 2411/1971) are dissolved in 20 ml. anhydrous acetonitrile, cooled to 0° C. and mixed with 1.8 ml. N-carbonylsulphamoyl chloride in 20 ml. acetonitrile. After a reaction period of about 1 hour, a solution of 3.4 g. potassium hydroxide in 34 ml. water is added thereto and the reaction mixture then stirred for 1 hour at ambient temperature. After evaporating the solvent, the residue is taken up in 200 ml. 2 N hydrochloric acid and extracted with methylene chloride. From the methylene chloride extract there are obtained 4.8 g. (45% of theory) 4-benzyloxy-3-aminocarbonylindole, which is recrystallized from ethyl acetate; m.p. 176° C.

EXAMPLE 7

4-Benzyloxy-3-cyanoindole 2.2 g. 4-Benzyloxyindole in 10 ml. acetonitrile are mixed at 0° C. with 0.9 ml. N-carbonylsulphamoyl chloride in 10 ml. acetonitrile. After 1 hour, 1.4 ml. triethylamine in 5 ml. acetonitrile is added dropwise thereto, whereafter the reaction mixture is stirred for 2 hours at ambient temperature and then stirred into an ice-cold aqueous solution of sodium bicarbonate. The mixture is then extracted with diethyl ether and the ethereal solution evaporated to give 1 g. (40% of theory) 4-benzyloxy-3-cyanoindole; m.p. 139°–141° C.

EXAMPLE 8

4-(2,3-Epoxypropoxy)-3-cyanoindole 7.7 g. 4-(2,3-Epoxypropoxy)-indole (see Helv. Chim. Acta, 54, 2411/1971) are dissolved in 150 ml. nitromethane and mixed, while cooling to 0° to 5° C., with 3.9 ml. N-carbonylsulphamoyl chloride in 15 ml. nitromethane. After a reaction period of 30 minutes, 3.7 ml. dimethylformamide are added thereto, the pH is adjusted to 9 with triethylamine and evaporated in a vacuum. The residue is taken up with ethyl acetate and purified over a silica gel column with ethyl acetate. The ethyl acetate eluate is shaken out with water, dried with anhydrous sodium sulphate and filtered off with suction. After removing the solvent, diethyl ether is added thereto, followed by suction filtration. There are obtained 4.6 g. (54% of theory) 4-(2,3-epoxypropoxy)-3-cyanoindole; m.p. 116°–120° C.

The following compounds are obtained in an analogous manner:

| | designation | yield | m.p. (solvent) |
|---|---|---|---|
| (a) | 4-(2,3-epoxypropoxy)-2-acetoxymethyl-3-cyanoindole from 4-(2,3-epoxypropoxy)-2-acetoxymethylindole | 73 | 113–115 (diethyl ether) |
| (b) | 4-(2,3-epoxypropoxy)-2-methyl-3-cyanoindole from | 57 | 137–138 (diethyl ether) |

| designation | yield | m.p. (solvent) |
|---|---|---|
| 4-(2,3-epoxypropoxy)-2-methylindole (see lit. ref. in Example 8) | | |
| (c) 4-(2,3-epoxypropoxy)-3-cyano-6-methylindole from 4-(2,3-epoxypropoxy)-6-methylindole (see Fed. Rep. of Germany Pat. Specn. No. 2508251) | 60 | oil |
| (d) 4-(2,3-epoxypropoxy)-3-cyano-6-t-butylindole from 4-(2,3-epoxypropoxy)-6-t-butylindole | 70 | oil |

EXAMPLE 9

4-Benzyloxy-3-cyanoindole

A solution of 1 mmol (2.2 g.) 4-benzyloxyindole in 20 ml. anhydrous methylene chloride is added dropwise at −40° C. under an atmosphere of nitrogen to a freshly prepared solution of 2.5 mmol triphenylphosphine thiocyanate (see Tetrahedron Letters, 1977, p. 4417) and the reaction mixture then stirred for 5 hours at this temperature, whereafter it is allowed to warm up to ambient temperature and further stirred overnight. After neutralization with triethylamine, the reaction mixture is evaporated in a vacuum and the residue purified over a column of silica gel. After removal of the solvent, there is obtained 1.5 g. (60% of theory) 4-benzyloxy-3-cyanoindole; m.p. 138°–140° C.

It will be appreciated that the instant specification and examples are set forth by way of illustration and not limitation, and that various modifications and changes may be made without departing from the spirit and scope of the present invention.

We claim:

1. An indole of the formula

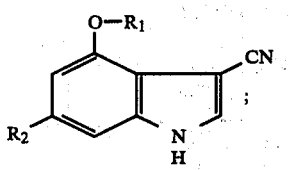

in which $R_1$ is a hydrogen atom, a phenyl-$C_{1-4}$-alkyl radical or a radical of the formula

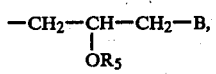

B is a chlorine or bromine atom, or a mesyloxy or tosyloxy radical, or together with $R_5$ is a valency bond, $R_5$ is a hydrogen or an acetyl, formyl or benzoyl radical, or together with B is a valency bond, and $R_2$ is a hydrogen atom or $C_{1-6}$-alkyl radical.

2. A compound according to claim 1, wherein such compound is 4-hydroxy-3-cyanoindole of the formula

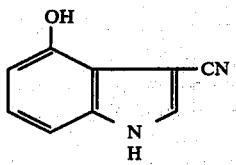

3. A compound according to claim 1, wherein such compound is 4-(2,3-epoxypropoxy)-3-cyanoindole of the formula

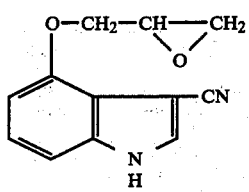

4. A compound according to claim 1, wherein such compound is 4-benzyloxy-3-cyanoindole of the formula

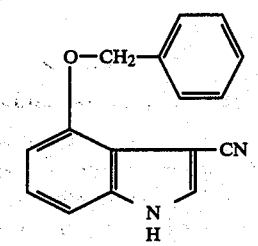

5. A compound according to claim 1, wherein such compound is 4-(2,3-epoxypropoxy)-3-cyano-6-methylindole of the formula

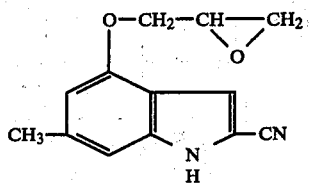

6. A compound according to claim 1, wherein such compound is 4-(2,3-epoxypropoxy)-3-cyano-6-t-butylindole of the formula

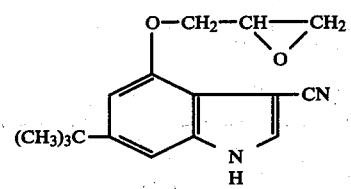

* * * * *